(12) United States Patent
Yuds et al.

(10) Patent No.: US 10,515,534 B1
(45) Date of Patent: Dec. 24, 2019

(54) BLOOD TREATMENT MACHINE WITH BLOOD PRESSURE MEASUREMENT NOTIFICATION

(71) Applicant: Fresenius Medical Care Holdings, Inc., Waltham, MA (US)

(72) Inventors: David Yuds, Hudson, NH (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/012,360

(22) Filed: Jun. 19, 2018

(51) Int. Cl.
*G08B 21/00* (2006.01)
*G08B 21/24* (2006.01)
*A61M 1/26* (2006.01)

(52) U.S. Cl.
CPC ............ *G08B 21/24* (2013.01); *A61M 1/267* (2014.02); *A61M 2205/3344* (2013.01); *A61M 2205/3569* (2013.01); *A61M 2205/502* (2013.01); *A61M 2205/581* (2013.01); *A61M 2205/582* (2013.01); *A61M 2205/583* (2013.01); *A61M 2205/584* (2013.01); *A61M 2205/587* (2013.01)

(58) Field of Classification Search
CPC ............ G08B 21/24; G05B 1/01; A61B 5/177
USPC ............. 340/679, 605, 618, 521, 5.25, 5.67; 210/85, 87, 650, 741
See application file for complete search history.

(56) References Cited

U.S. PATENT DOCUMENTS

| | | |
|---|---|---|
| 3,861,698 A | 1/1975 | Greig |
| 5,161,538 A | 11/1992 | Fukura et al. |
| 5,690,831 A | 11/1997 | Kenley et al. |
| 5,772,624 A | 6/1998 | Utterberg et al. |
| 5,895,368 A | 4/1999 | Utterberg |
| 6,165,149 A | 12/2000 | Utterberg et al. |
| 6,290,665 B1 | 9/2001 | Utterberg |
| 6,387,069 B1 | 5/2002 | Utterberg |
| 6,620,119 B1 | 9/2003 | Utterberg et al. |

(Continued)

FOREIGN PATENT DOCUMENTS

| | | |
|---|---|---|
| CA | 2181024 | 1/1997 |
| EP | 0754468 | 1/1997 |

(Continued)

OTHER PUBLICATIONS

British Hypertension Society, Standard Operating Procedure for Ambulatory Blood Pressure Monitoring (ABPM)—This includes day & night time instructions; 3 pages.

(Continued)

*Primary Examiner* — Tai T Nguyen
(74) *Attorney, Agent, or Firm* — Fish & Richardson P.C.

(57) ABSTRACT

A system for blood treatment that includes a blood treatment machine. The blood treatment machine includes a receiver, a user interface configured to display information related to the blood pressure data received by the receiver, and a controller. The controller is configured to generate a notification to notify a user of an upcoming blood pressure measurement before the blood pressure measurement occurs. The blood treatment machine also includes a blood pressure monitoring device connected to the blood treatment machine, the blood pressure monitoring device configured to send signals containing blood pressure information to the receiver of the blood treatment machine.

22 Claims, 6 Drawing Sheets

(56) References Cited

U.S. PATENT DOCUMENTS

| | | |
|---|---|---|
| 6,649,063 B2 | 11/2003 | Brugger et al. |
| 6,666,839 B2 | 12/2003 | Utterberg et al. |
| 7,166,084 B2 | 1/2007 | Utterberg |
| 7,214,312 B2 | 5/2007 | Brugger et al. |
| 7,226,538 B2 | 6/2007 | Brugger et al. |
| 7,387,734 B2 | 6/2008 | Felding |
| 7,419,597 B2 | 9/2008 | Brugger et al. |
| 7,588,684 B2 | 9/2009 | Brugger et al. |
| 7,780,848 B2 | 8/2010 | Kim et al. |
| 7,790,043 B2 | 9/2010 | Brugger et al. |
| 8,409,441 B2 | 4/2013 | Wilt |
| 8,491,518 B2 | 7/2013 | Schnell et al. |
| 8,608,680 B2 | 12/2013 | Hasegawa |
| 8,721,884 B2 | 5/2014 | Wilt et al. |
| 9,480,784 B2 | 11/2016 | Kelly et al. |
| 9,555,179 B2 | 1/2017 | Wilt et al. |
| 2002/0151834 A1 | 10/2002 | Utterberg |
| 2003/0100858 A1 | 5/2003 | Utterberg et al. |
| 2005/0131331 A1 | 6/2005 | Kelly et al. |
| 2006/0289342 A1* | 12/2006 | Sugioka ............ A61M 1/16 210/85 |
| 2007/0106196 A1 | 5/2007 | Utterberg |
| 2008/0065006 A1* | 3/2008 | Roger ............ A61M 1/16 604/65 |
| 2009/0124963 A1 | 5/2009 | Hogard et al. |
| 2009/0216134 A1 | 8/2009 | Hollinger et al. |
| 2013/0310726 A1 | 11/2013 | Miller et al. |
| 2014/0158589 A1 | 6/2014 | Furuhashi et al. |
| 2016/0030657 A1 | 2/2016 | Kelly et al. |
| 2016/0074571 A1 | 3/2016 | Kopperschmidt |
| 2016/0199559 A1* | 7/2016 | Glaser ............ A61M 1/16 210/321.71 |
| 2016/0199562 A1 | 7/2016 | Parisotto et al. |
| 2016/0220748 A1* | 8/2016 | Pouchoulin ......... A61M 1/3621 |
| 2017/0293727 A1 | 10/2017 | Klaasen et al. |
| 2017/0326284 A1* | 11/2017 | Dulsner ............ G06F 19/3481 |
| 2017/0340801 A1* | 11/2017 | Roger ............ A61M 1/3656 |
| 2018/0185566 A1* | 7/2018 | Hakansson ............ A61M 1/16 |

FOREIGN PATENT DOCUMENTS

| | | |
|---|---|---|
| EP | 2752210 | 7/2014 |
| JP | H09122230 | 5/1997 |
| JP | 2013-27633 | 2/2013 |
| WO | WO 2016/087476 | 6/2016 |

OTHER PUBLICATIONS

Omron Instruction Manual, Wrist Blood Pressure Monitor with Advanced Positioning Sensor (APS); Model HEM-637, 2006, 17 pages.

custo med GmbH, Operating Manual ABPM with custo screen 100/200 and custo diagnostic, Feb. 12, 2010, 56 pages.

Central Sydney Cardiology, Patient Information Sheet, Ambulatory [24hr] Blood Pressure recording, 1 page.

"5008 Hemodialysis system: Operation Instructions," Fresenius Medical Care, Edition 10/08.13, Part No. M518941, 382 pages.

"Set-Up and Prime (con't)," Phoenix Training Manual, Gambro Lundia AB 306050288, Rev. G., 2007, pg. 6.

"Section 5—Dialysis Operation: 5.10—5.10.1," Phoenix Operator Manual, Rev. A., pp. 52-53.

International Search Report and Written Opinion in Application No. PCT/US2018/042852, dated Nov. 12, 2018, 11 pages.

International Search Report and Written Opinion in Application No. PCT/US2019/037300, dated Oct. 2, 2019, 11 pages.

* cited by examiner

BLOOD TREATMENT MACHINE WITH BLOOD PRESSURE MEASUREMENT NOTIFICATION

TECHNICAL FIELD

This disclosure relates to a blood treatment machine with blood pressure measurement notification.

BACKGROUND

Blood treatment is recommended to patients who cannot sufficiently clear their blood of toxins. Blood treatment often occurs at a clinic that operates multiple blood treatment machines. However, at-home blood treatment machines are also available. At a blood treatment clinic, a user or operator prepares the blood treatment machine for blood treatment, attaches the patient to the blood treatment machine prior to treatment, and detaches the patient from the blood treatment machine when the blood treatment is completed. During blood treatment, the operator routinely checks the patient to ensure the blood treatment machine is operating properly. The blood treatment machine is also typically configured to automatically monitor various machine and patient parameters during treatment. One such patient parameter that is typically monitored is blood pressure (BP). Each blood treatment machine typically also has programmable alarms that notify the operator when a measurement is outside of a programmed range. Notifying the operator in this way allows the operator to address the alarm condition.

SUMMARY

The foregoing and other embodiments can each optionally include one or more of the following features, alone or in combination.

In a first aspect, a system for blood treatment comprises a blood treatment machine comprising a receiver, a user interface configured to display information related to the blood pressure data received by the receiver, and a controller configured to generate a notification to notify a user of an upcoming blood pressure measurement before the blood pressure measurement occurs. A blood pressure monitoring device connected to the blood treatment machine is configured to send signals containing blood pressure information to the receiver of the blood treatment machine.

In some embodiments, a blood pump is configured to pump blood through an extracorporeal blood circuit when the extracorporeal blood circuit is connected to the blood treatment machine.

In some embodiments, the blood pressure monitoring device and blood treatment machine are electronically connected, and the blood pressure monitoring device is operable to send signals to the blood treatment machine, using an electronic connector.

In some embodiments, the blood pressure monitoring device and the blood treatment machine are wirelessly connected, and the blood pressure monitoring device is operable to transmit signals to a signal receiver on the blood treatment machine, using a signal transmitter of the blood pressure monitoring device.

In some embodiments, the signals from the blood pressure monitoring device indicate that the blood pressure monitoring device will measure blood pressure in a defined amount of time, for example, less than one minute.

In some embodiments, the signals from the blood pressure monitoring device indicate that the blood pressure monitoring device is measuring blood pressure.

In some embodiments, the system further comprises a second interface connected the blood treatment machine. The second interface may be a smartphone, a tablet, or a computer. The second interface and the blood treatment machine can be wirelessly connected.

In some embodiments, the second interface comprises a processor, a signal transmitter, and a signal receiver, wherein the signal transmitter of the second interface is operable to send signals to the blood treatment machine, and the signal receiver of the second interface is operable to receive signals from the blood treatment machine. The processor of the second interface can be configured to generate an alert, for example, a visual, auditory, or vibrational alert. In some embodiments, at least part of the second interface is configured to vibrate when the processor generates the alert. The alert of the second interface can indicate an upcoming blood measurement will occur in an amount of time, for example, less than one minute.

In some embodiments, the controller is configured to generate the notification based on data received from a timer of the blood treatment machine.

In some embodiments, the controller is configured to generate the notification based on data received from a timer of the blood monitoring device.

In some embodiments, the controller is configured so that the operator can see parameters of the notification.

In a second aspect, a blood treatment machine comprises a receiver configured to receive blood pressure data from a blood pressure monitor when the blood pressure monitoring device is connected to the blood treatment machine, a user interface configured to display information related to the blood pressure data received by the receiver, and a controller configured to generate a notification to notify a user of an upcoming blood pressure measurement before the blood pressure measurement occurs.

In some embodiments, the controller is configured to generate a visual notification. The visual notification may be displayed on the user interface. The visual notification may be, for example, at least one light, and generating the visual notification can include turning on the at least one light. The light may flash or blink.

In some embodiments, the controller is configured to generate an auditory notification. The auditory notification can be distinct from other alarms emitted by the blood treatment machine, for example, a pulsing sound. The blood treatment machine may further comprise a speaker configured to emit the auditory notification.

In some embodiments, the blood treatment machine is configured to connect to a blood pressure monitoring device. The blood pressure treatment machine and the blood pressure monitoring device may be electronically or wirelessly connected.

In some embodiments, blood treatment machine is configured to connect to a second interface. The blood treatment machine and the second interface may be configured to be wirelessly connected.

In a third aspect, a method of notifying an operator of a blood treatment machine that a blood pressure measurement is about to occur comprises placing a blood pressure monitoring device for measuring blood pressure on a patient, notifying the operator of the blood treatment machine that the blood pressure measurement is about to occur, and measuring the blood pressure of the patient.

In some embodiments, the blood pressure monitoring device sends signals to a blood treatment machine. The signals may be sent a defined amount of time before the blood pressure monitoring device measures blood pressure, for example, less than one minute.

In some embodiments, notifying the operator includes receiving a signal from the blood pressure monitoring device and generating a notification on a blood treatment machine.

In some embodiments, notifying the operator further includes sending a signal from the blood treatment machine to a connected second interface and producing an alert on the second interface.

In some embodiments, notifying the operator includes transmitting a signal from the blood pressure monitoring device to the blood treatment machine, sending a signal from the blood treatment machine to a second interface, and generating an alert on the second interface.

Particular embodiments of the subject matter described in this specification can be implemented so as to realize one or more of the following advantages. A severe decrease in blood pressure during dialysis can lead to muscle cramps nausea and vomiting, or dizziness. Thus, the blood pressure of a patient is routinely monitored during blood treatment. By notifying the operator prior to taking a blood pressure measurement, the operator can monitor the patient during the blood pressure measurement and thus better assess the patient's condition. Alarm fatigue occurs when an operator becomes more lax in responding to alarms due to a high frequency of alerts from the blood treatment machines. The notification may prevent alarm fatigue by generating a notification that is unique and distinct from other alerts and notifications of the blood treatment machine. The notification can be either silent or a pleasing sound so other patients and operators are not annoyed. The clinic manager may even upload a custom tone of their choosing to personalize the notification for their own clinic. This tone could even be changed throughout the year to match festive calendars or moods. The notification can be sent to a portable interface to ensure the operator receives the notification even if the operator is not in the vicinity of the blood treatment machine.

Additionally, the blood treatment machine can generate a quality of care record that can help to indicate the attentiveness of the clinic's staff towards a patient. For example, the machine could compile a record of blood pressure notifications that are manually cleared versus ignored or could show the average time elapsed between an alert and clinical attention (i.e., notification confirmation).

The notifications can also provide extra time for a clinician to place the blood pressure cuff and confirm the correct placement with a confirmation mechanism (e.g., button or spoken command). This can be particularly useful when patients remove the blood pressure cuff between measurements.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

A blood treatment system is disclosed that is configured to notify an operator or user of an upcoming blood pressure measurement. The system includes a blood pressure monitoring device connected blood treatment machine. The blood treatment machine is configured to notify the operator of an upcoming blood pressure measurement. The notification can be customized during setup, while inputting the ranges for blood pressure alarms. Prior to measuring the blood pressure, the system can generate a notification, distinct from other alarms or notifications, regarding an upcoming blood pressure measurement. The system may further include a second interface connected to the blood treatment machine that is portable and configured to notify the operator of an upcoming blood pressure measurement. Thus, the system, with the second interface, alerts the operator when the operator is away from the blood treatment machine. Notifying the operator or user of the upcoming blood pressure measurement allows the operator or user to go to the machine and monitor the patient during the blood pressure measurement.

Figure 1:
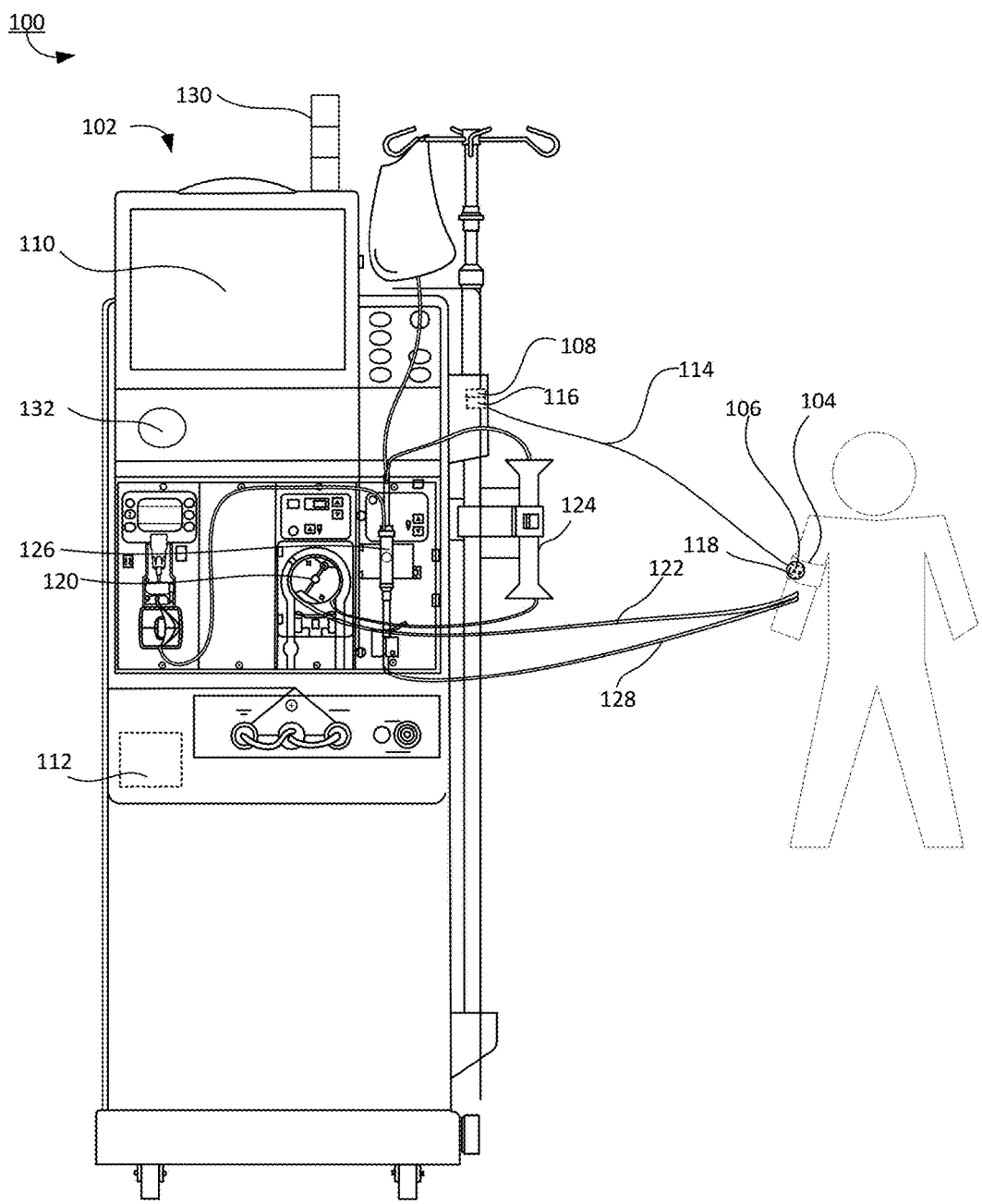
FIG. 1 shows a blood treatment system including a blood treatment machine and a blood pressure monitoring device where the blood treatment machine is configured to notify an operator of an upcoming blood pressure measurement.

FIG. 1 shows a blood treatment system 100 that includes a blood treatment machine (e.g., hemodialysis machine) 102 and a blood pressure monitoring device 104, connectable to blood treatment machine 102. Blood pressure monitoring device 104 includes a signal transmitter 106 configured to send signals containing blood pressure data to blood treatment machine 102. Blood treatment machine 102 includes a receiver 108, a user interface 110 (e.g. touchscreen), and a controller 112. Signal receiver 108 is configured to receive blood pressure data from blood pressure monitoring device 104, when blood treatment machine 102 and blood pressure monitoring device 104 are connected. In FIG. 1, the blood treatment machine 102 and blood pressure monitoring device 104 are connected electronically, using an electronic connector 114. User interface 110 is mounted on or integrated in blood treatment machine 104 and is operably controlled by controller 112. Blood treatment machine 102 is programmable to intervally prompt the connected blood pressure monitoring device 104 to take blood treatment measurements by transmitting a signal from a signal transmitter 116 of the blood treatment machine to signal receiver 118 of the blood pressure monitoring device. User interface 110 is configured to display information related to the blood pressure data received by receiver 108. Prior to taking the blood pressure measurement, controller 112 of blood treatment machine 102 will generate a notification to notify the operator that the blood pressure measurement is about to occur. The notification may be visual, auditory, and/or vibrational.

In operation, a blood pump 120 of blood treatment machine 102 is operated to pump blood through an extra-corporeal circuit 120 connected to blood treatment machine 102. More specifically, blood pump 118 draws blood out of the patient via an arterial patient line 122 and forces the blood through a blood chamber of a dialyzer 124. As the blood passes through the blood chamber of dialyzer 124, dialysate passes through a dialysate chamber of dialyzer 124, so that the blood is cleared of toxins. The cleansed blood then flows through a venous air trap 126 where any air in the blood is collected and is returned to the patient via a venous patient line 128. As this occurs, controller 112 maintains a repetitive timer to, among other things, allow periodic blood pressure measurements to be automatically carried out. When the timer expires, controller 112 prompts blood pressure monitoring device 104 to measure the blood pressure of the patient. During setup, the operator may opt for a notification to alert the operator when the blood pressure measurement is about to be taken. The operator, for example, may set the notification time to 10 seconds prior to measuring the blood pressure. Therefore, 10 seconds before the timer of blood treatment machine 102 expires, controller 112 generates a notification alerting the operator that the blood pressure measurement will begin in 10 seconds, i.e., the set notification time. The timer expires and controller 112 sends the prompt to begin the blood pressure measurement via signal transmitter 116 and electronic connecter 114. Blood pressure monitoring device 104 receives the prompt via signal receiver 118 and begins to measure blood pressure.

After the blood pressure measurement is completed, blood pressure data is transmitted from blood pressure monitoring device 104 to blood treatment machine 102 via signal transmitter 106 and electronic connecter 114. The transmission of blood pressure data indicates to blood treatment machine 102 that blood pressure monitoring device 104 has finished measuring blood pressure. Signal receiver 108 receives the blood pressure data and user interface 110 then displays the blood pressure data. The notification may terminate as the timer expires, or continue while measuring the blood pressure, terminating at completion of measuring the blood pressure. Additionally, the operator may confirm receipt of the notification on user interface 110 to terminate the notification. The timer resets to the original value and begins to count down again. As before, the notification indicating an upcoming blood pressure measurement will generate 10 seconds prior to the timer expiration.

As shown in FIG. 1, blood treatment machine 102 also includes a light column 130 and a speaker 132. The light column 130 contains lights that may also generate a visual notification. Such a visual notification may flash and/or may include a variety of colors and lights. The light color notifying the operator of the blood pressure measurement may be different from other light colors used for alarms. For instance, the visual notification used for notifying the operator of a blood pressure measurement may be a blue light or alternating yellow and green lights, while an alarm may use a red light. The speaker may be configured to generate an auditory notification. Such an auditory notification could be a beep sound, distinct from the alarm sounds of the machine. The sound may alternatively be a verbal countdown, indicating the time remaining before the blood pressure measurement will be taken. The auditory notification may emit a beeping sound that increases in frequency as specified time 606 decreases. Alternatively, the vibration alarm may also pulse in increasing frequency as specified time 606 decreases. A combination of notification types, such as visual and auditory notifications, may also be used to notify the operator of an upcoming blood pressure measurement.

Figure 2:
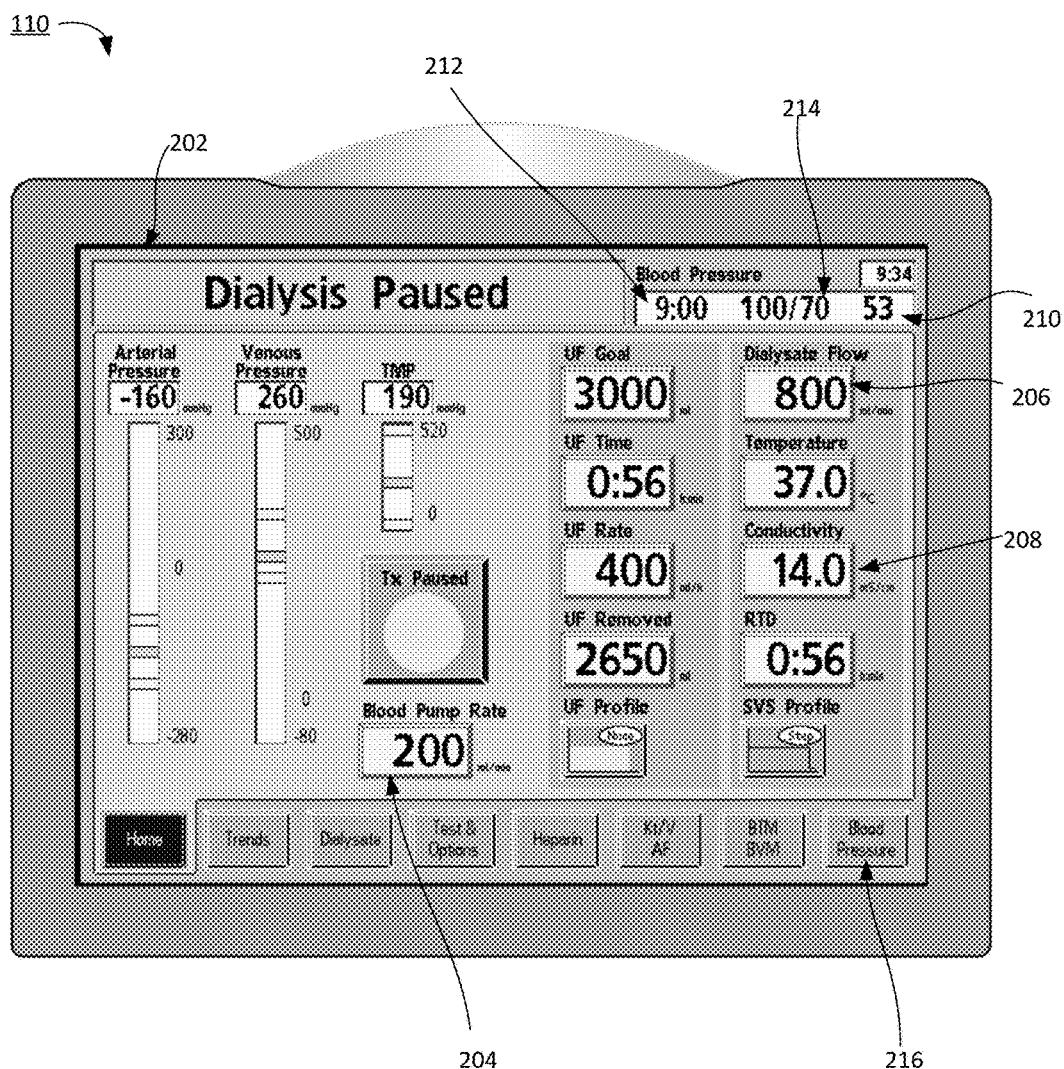
FIG. 2 shows a home screen of a user interface of the blood treatment system shown in FIG. 1.

FIG. 2 illustrates a home screen 202 of user interface 110 during a blood treatment. The operator may cause user interface 110 to display different windows by selecting different tabs on the bottom of the screen. In FIG. 2, home screen 202 is selected. Home screen 202 displays information regarding the blood treatment, such as blood pump rate 204, dialysate flow rate 206, and conductivity levels 208. Additionally, user interface 110 displays blood pressure information 210. Home screen 202 in FIG. 2 displays blood pressure information 210 in the upper right hand corner; however, in other embodiments, the information may be displayed in a different location on the home screen or on a different window tab. The blood pressure information includes the time 212 that the most recent blood pressure measurement was taken, the blood pressure 214 of the most recent measurement, and the heart rate or pulse 216 of the patient during that measurement. The blood pressure measurement intervals and additional notification features are customizable on Blood Pressure tab 216.

Figure 3:
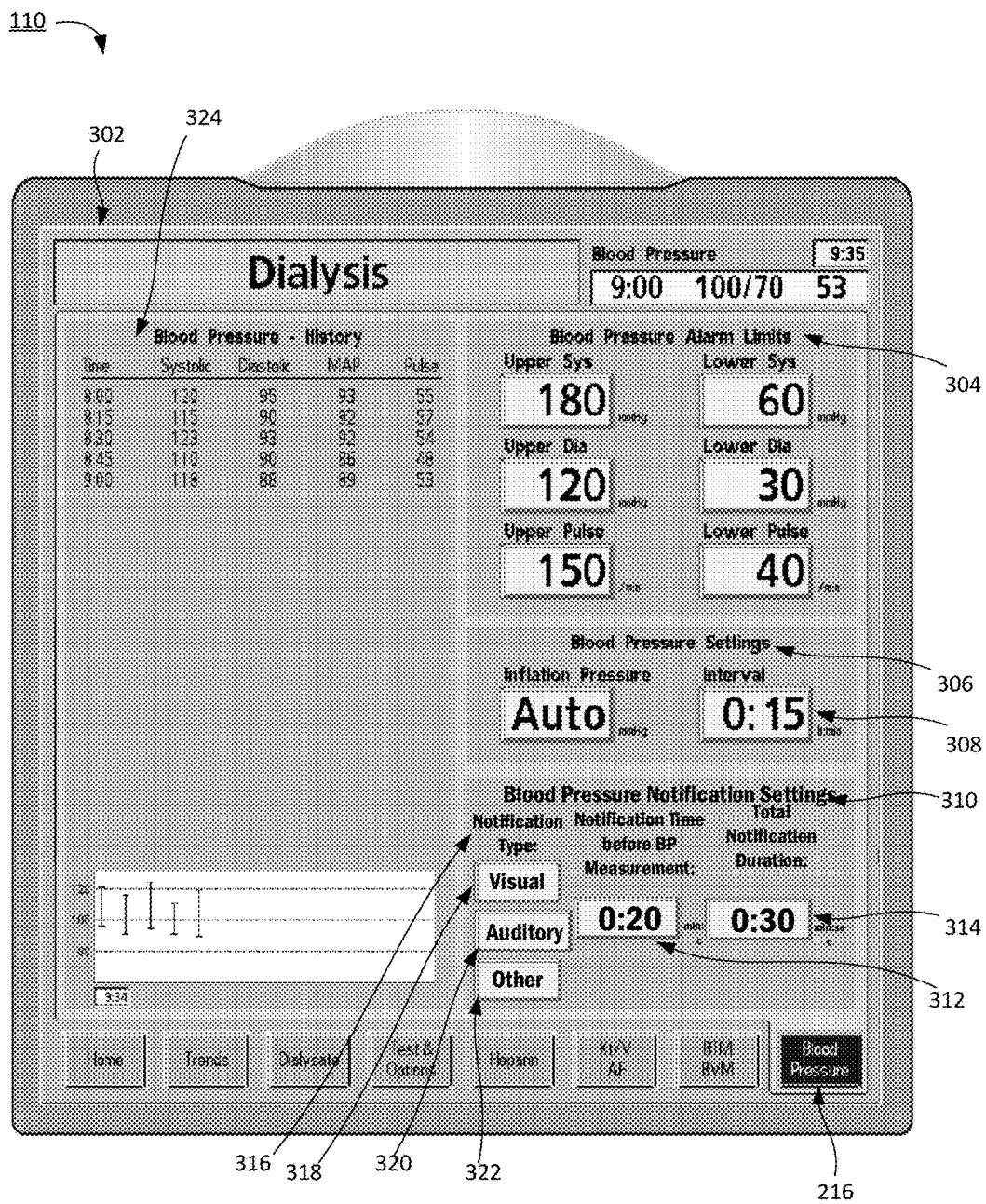
FIG. 3 shows a blood pressure settings screen of the user interface of the blood treatment system shown in FIG. 1.

User interface 110 displays a pressure window 302 when Blood Pressure tab 216 is selected, as shown in FIG. 3. Blood pressure window 302 is used to set parameters regarding blood pressure alarms and blood pressure notifications. Blood pressure alarms occur after taking the blood pressure measurement and, when generated, indicate that the measured blood pressure is outside a predefined range. The range can be set in Blood Pressure Alarm Limits section 304. The intervals at which blood pressure is measured are defined in Blood Pressure Settings section 306 by inputting a time into the Interval box 308. The intervals are inputted as hours:minutes. Under Blood Pressure Settings section 306 is Blood Pressure Notification Settings section 310. In Blood Pressure Notification Settings section 310 the operator can define the time at which the controller 112 generates the notification by inputting a time into "Notification Time before BP Measurement" box 312. The duration of the notification is also customizable by the operator by inputting a time in "Total Notification Duration" box 314. In FIG. 3, the blood pressure is set to be measured every 15 minutes as indicated by Interval box 308. Controller 112 will generate the notification 20 seconds before the 15-minute interval timer expires. Additionally, the notification continues for 30 seconds, i.e., the notification will remain 10 seconds into measuring the blood pressure before terminating. When "Notification Time before BP Measurement" box 312 and "Total Notification Duration" box 314 display equal times, the notification will terminate when controller 112 sends the prompt to begin measuring blood pressure, i.e., when the timer expires. When "Notification Time before BP Measurement" box 312 displays a time greater than "Total Notification Duration" box 314, the notification will continue for a time after controller 112 sends the prompt to begin measuring blood pressure. When "Notification Time before BP Measurement" box 312 displays a time less than "Total Notification Duration" box 314, the notification terminates before controller 112 sends the prompt.

Additionally, Blood Pressure Notification Settings section 310 includes a Notification Type column 316. The notification can be one or a combination of notification types. In FIG. 3, a user may choose a type of notification by selecting "Visual" box 318 and/or "Auditory" box 320. Additional types of notifications, such as vibrational notifications or notifications that generate external from the blood treatment machine can be chosen by first selecting "Other" box 322. Boxes 318, 320, and 322 may lead an operator to a list of available notifications for the selected notification type.

Selecting the "Visual" box 318 leads the operator to a list with multiple forms of visual notifications. The visual notification list may include an LED visual notification option, which generates a flashing light on light column 122, and a user interface notification option, which generates a message on the user interface 110. After selecting the LED notification off of the visual notification list, a second menu may appear that allows the user to further customize the LED notification. The second menu may include the flashing frequency, the LED color, and optional second, third, and fourth LED color, the flash length, and the brightness of the LED. The flashing frequency can be set to high, medium, low, and gradual increase. The gradual increase option will increase the frequency of the flash as the notification time decreases. The light column 130 may include a variety of colored LEDs. The color options include all available LED colors on the light column 130. The flash length determines the length of time the LED is on and the length of time the LED is off. The brightness option allow the operator to choose how much light the LEDs emit. The operator uses a slidable toggle to select a brightness or the can choose from a preset choice of low, medium, or high.

Selecting the "Auditory" box 320 leads the operator to a list with multiple forms of auditory notifications. The list may include a verbal countdown notification, which generates a voice counting down numerically notifying the operator of the remaining time until a blood pressure measurement will be taken. The voice defaults to the language currently used on the machine and will change if the overall language preference is also changed. The list may also include a beeping notification, leading the operator to a second menu. The customizable features of the beeping notification option are listed in the second menu. The operator may select the type of beep. The types of beeps include a click, tick tock noise, a beep noise, or a siren. The operator may select the beeping tone from high, medium, and low. The operator may also select the beeping frequency from high, medium, low, and gradual increase. The gradual increase frequency increases the beeping noise as the notification time decreases. The operator may further select the beeping volume from a choice of high, medium, low, and gradual increase. The gradual increase in volume increases the beeping noise as the notification time decreases.

Selecting the "Other" box 322 leads the operator to a list with multiple forms of vibrational and external notifications. The vibrational notification list may include a pulsing vibrational notification option and a steady vibrational notification option. The operator may select the vibrational pulse frequency from high, medium, low, and gradual increase. The gradual increase setting will increase the frequency of the vibrational pulses as the notification time decreases. The "Other" category may also list external notification options for connected devices. For example, the list may include all connected external devices that are configured to generate a notification. For example, if the blood pressure monitoring device is configured to generate a notification, the term "BP monitor" is listed as a connected external device.

FIG. 3 also shows a Blood Pressure History section 324 that includes previous blood pressure measurement information and a visual graph to plot blood pressure trends.

Figure 4:
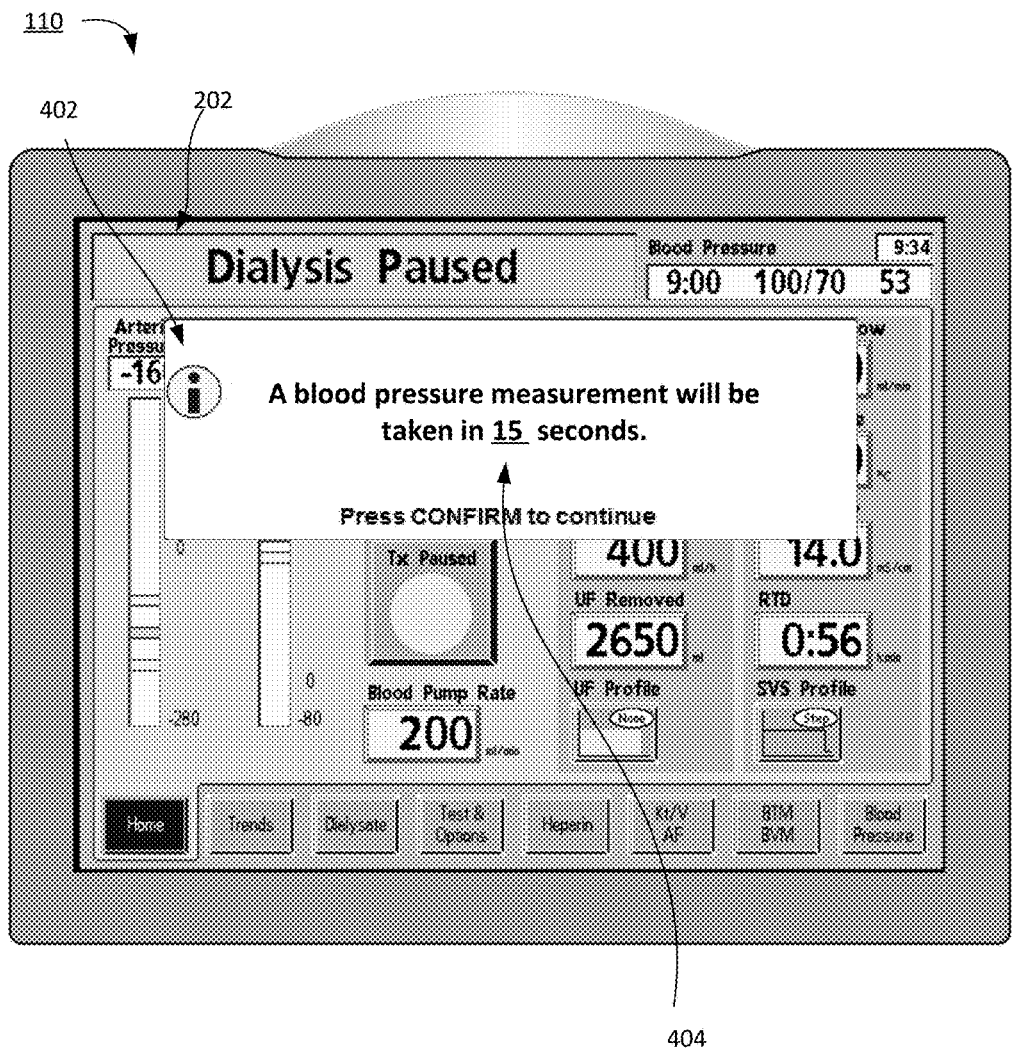
FIG. 4 shows a blood pressure measurement notification on the home screen of FIG. 2.

FIG. 4 shows home screen 202 on which a visual notification 402 is displayed. Visual notification 402 shows a duration of the notification 404 that indicates an upcoming blood pressure measurement. Visual notification 402 displays the notification duration 404 and prompts the operator to confirm receipt of the notification. Confirming will clear the notification 402. If confirmed early, the notification will clear but will not expedite blood pressure measurement. If left unconfirmed, notification will terminate at the end of the count down. Leaving the notification unconfirmed does not delay blood pressure measurement. Visual notification 402 may blink to attract the attention of the operator. For example, visual notification 402 may flash for the last 5 seconds of notification duration 404. As discussed above, other types of visual notifications, auditory notifications, and/or other forms of notifications may be used in combination with the visual notification 402.

Figure 5:
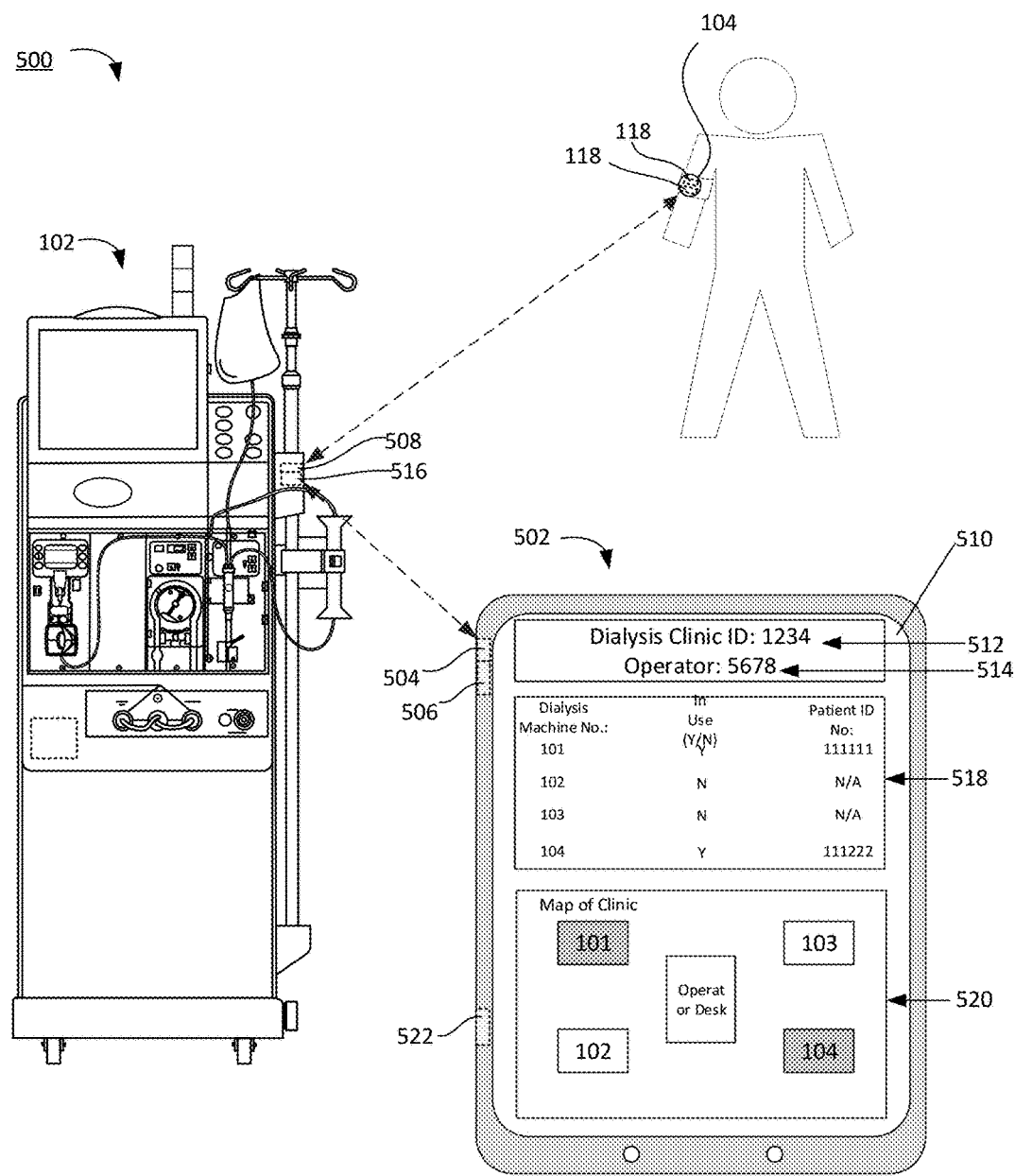
FIG. 5 shows a blood treatment system connected to a second interface.

While the various notification devices discussed above are all part of blood treatment machine 102, notification devices separate from the blood treatment machine can alternatively or additionally be used. Similarly, while blood pressure monitoring device 104 has been described as being connected by wire to blood treatment machine 102, in certain implementations, wireless connections can be used. FIG. 5 shows a blood treatment system 500 with a second interface 502 wirelessly connected to blood treatment machine 102. Additionally, blood treatment machine 102 is wirelessly connected to blood pressure monitoring device 104. Second interface 502 may be a tablet, a smart phone, a computer, or any of various other types of mobile devices. Second interface 502 includes a wireless signal transmitter 504 and a wireless signal receiver 506. Second interface 502 is connectable to multiple blood treatment machines. Signal transmitter 504 is configured to send a signal to a wireless signal receiver 508 of blood treatment machine 102. Signal receiver 506 is configured to receive a signal from a wireless signal transmitter 516 of blood treatment machine 102. Second interface 502 shows a display 510 that is unique to a blood treatment clinic. The blood treatment clinic is identified with a Dialysis Display 512 and an operator is identified by an Operator ID 514. A first section 518 in display 510 lists information about all blood treatment machines in the clinic that are connected to second interface 502. The information in first section 518, includes the machine ID number, whether the machine is currently in use, and if in use, the patient ID of the patient receiving blood treatment. A second section 520 of display 510 shows a map of the clinic. The map shows the locations of connected blood treatment machines as well as the status of the blood treatment machines. The blood treatment machines performing blood treatment are shaded while the available blood treatment machines are kept unshaded. The blood treatment machines on the map are also labelled with the machine ID number.

In system 500, blood treatment machine 102 sends a signal to second interface 502 that indicates blood treatment machine 102 will send blood pressure monitoring device 104 a prompt to begin blood pressure measurement in a defined amount of time. Second interface 502 uses a processor 522 to generate an alert to notify the operator via second interface 502, of an upcoming blood pressure measurement. The alert may be visual, auditory, or vibration. An example of a visual alert on display 510 of second interface 502 is shown in FIG. 6.

Figure 6:
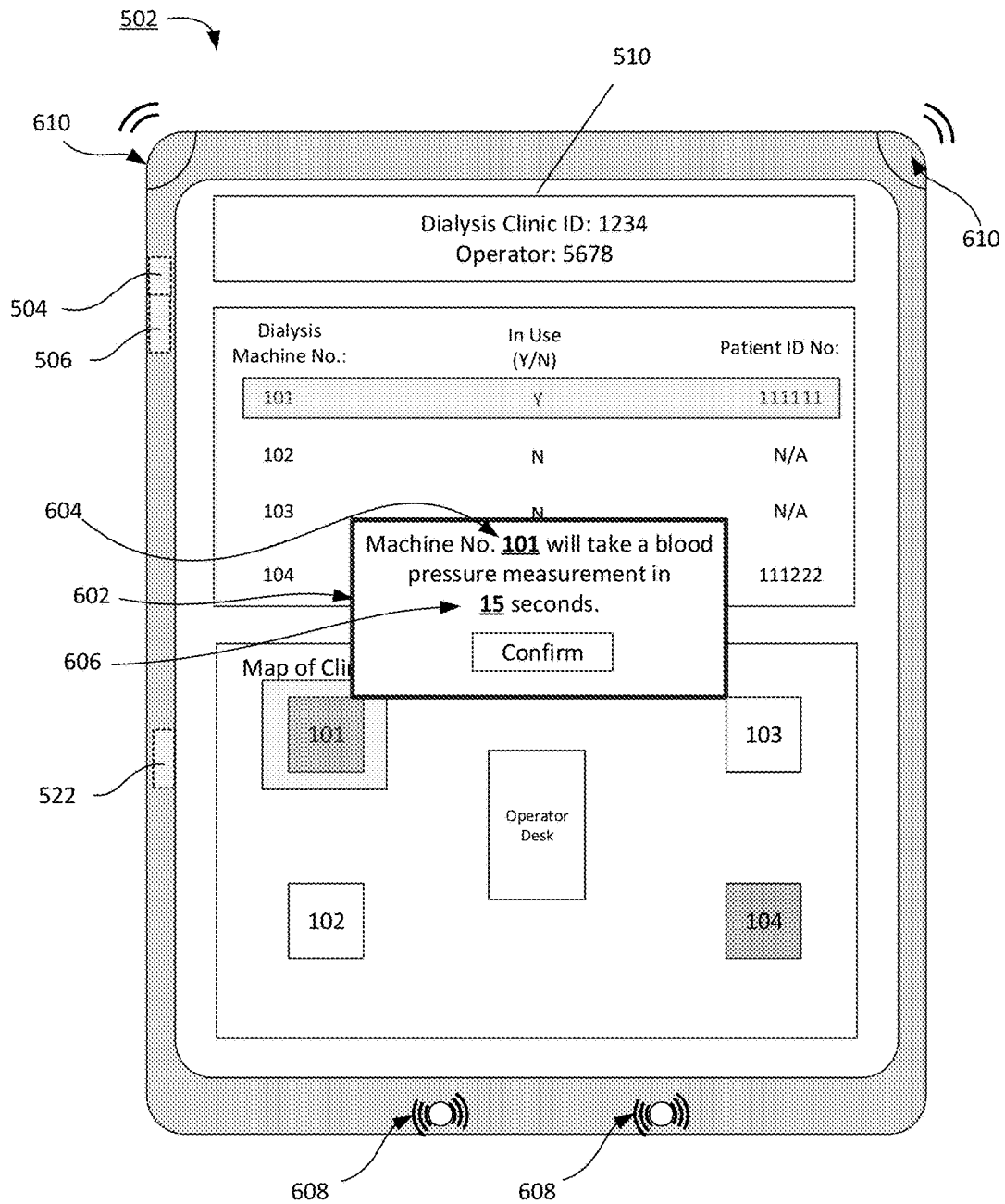
FIG. 6 shows the second interface of FIG. 5 displaying a blood pressure measurement alert.

FIG. 6 shows a visual alert 602 on the display 510. Visual alert 602 notifies the operator of a blood treatment machine ID 604 that will measure blood pressure in a specified amount of time 606. Processor 522 generates visual alert 602 when blood treatment machine 502 transmits a signal to signal receiver 506 of second interface 502. The signal contains blood treatment machine ID 604, specified time 606, and a type of alert for processor 522 to generate. Blood pressure machine ID 604 is highlighted in first section 518 and on second section 520 to further help the operator to identify blood treatment machine.

In FIG. 6, the alert is a visual alert 602; however, the second interface 502 may alternatively or additionally be configured to generate an alert that is auditory and/or vibrational. The second interface may include speakers 608 and/or may have vibrational sections (e.g., motors) 610 to alert the operator of an upcoming blood pressure measurement. The various types of visual, auditory, and vibration notifications described above in reference to FIG. 1 can be used with the alerts in second interface 502. Similarly the alert may also be a combination of visual, auditory, or vibration alerts.

In FIG. 6, the type of alert is determined by the signal sent by blood treatment machine 102. The type of alert is selected through the "Other" box 322 on user interface 110 of blood treatment machine 102. In alternative embodiments, the type of alert is selected through second interface 502.

During operations described above, both the blood treatment machine and the second interface notify the operator of an upcoming blood pressure measurement. The blood treatment machine 102 notifies the operator by generating a visual notification 402 in FIG. 4 and the blood pressure monitoring device 104 notifies the operator by generating a visual alert 602. Alternatively or additionally, the blood treatment machine 102 may use the light column 116 as a visual notification, the speaker as an auditory notification, or a combination thereof.

In another embodiment, only second interface 502 generates an alert to notify the operator of an upcoming blood pressure measurement. In this case, blood treatment machine 102 does not generate a notification. Alternatively, second interface 502 may be connected to blood treatment machine 102, but does not generate an alert, while blood treatment machine 102 does generate a notification.

While the second interface is described above as a tablet, it may be a smart phone, computer, or other portable device with a display, signal transmitter, signal receiver, and processor.

While the user interface is described above as a touchscreen, it may also be a conventional display with control buttons.

While the blood pressure notification systems has been described with respect to hemodialysis machines, it may be used in any of various other types of blood treatment machines, including hemofiltration machines, hemodiafiltration machines, peritoneal dialysis machines, etc.

In blood treatment systems 100, 500 of FIG. 1 and FIG. 5, blood pressure monitoring device 104 transmits a blood pressure measurement to blood treatment machine 102. In an alternative embodiment, the blood pressure monitoring device sends raw blood pressure data to blood treatment machine 102. In this case, blood treatment machine 102 receives the raw blood pressure data, processes the raw data using controller 112, determines the blood pressure measurement, and displays the blood pressure measurement on user interface 110.

In an alternative embodiment, the blood pressure monitoring device may also include a processor that controls an interval timer synchronized with the interval timer of a connected blood treatment machine. The blood pressure monitoring device begins measuring blood pressure when prompted by the processor of the blood pressure monitoring device. The blood pressure monitoring device then transmits the blood pressure measurement to the blood treatment machine. The processor of the blood pressure monitoring device may also be wirelessly connected to a second interface and configured to transmit a signal prior to prompting the blood pressure measurement. The signal, transmitting from the blood pressure monitoring device to receivers on the second interface and the blood treatment device, prompts the controller to generate a notification on the blood treatment machine and prompts a processor on the second interface to generate an alert on the second interface. The notification and alert notifies the operator of an upcoming blood pressure measurement. Alternatively, only the notification or only the alert may be generated.

Particular embodiments of the subject matter have been described. Other embodiments are within the scope of the following claims.

The invention claimed is:

1. A system for blood treatment, the system comprising:
a blood treatment machine comprising:
    a receiver,
    a user interface configured to display information related to the blood pressure data received by the receiver, and
    a controller configured to generate a notification, based on data received from a timer, to notify a user of an upcoming blood pressure measurement before the blood pressure measurement occurs; and
a blood pressure monitoring device connected to the blood treatment machine, wherein the blood pressure monitoring device is configured to send signals containing blood pressure information to the receiver of the blood treatment machine.

2. The system of claim 1, further comprising a blood pump configured to pump blood through an extracorporeal blood circuit when the extracorporeal blood circuit is connected to the blood treatment machine.

3. The system according to claim 1, wherein the blood pressure monitoring device and blood treatment machine are electronically connected and the blood pressure monitoring device is operable to send signals to the blood treatment machine, using an electronic connector.

4. The system according to claim 1, wherein the blood pressure monitoring device and the blood treatment machine are wirelessly connected, and the blood pressure monitoring device is operable to transmit signals to a signal receiver on the blood treatment machine, using a signal transmitter of the blood pressure monitoring device.

5. The system according to claim 1, wherein the signals from the blood pressure monitoring device indicate that the blood pressure monitoring device will measure blood pressure in a defined amount of time.

6. The system according to claim 5, wherein the defined amount of time less than one minute.

7. The system according to claim 1, wherein the signals from the blood pressure monitoring device indicate that the blood pressure monitoring device is measuring blood pressure.

8. The system according to claim 1, wherein the system further comprises a second interface connected the blood treatment machine.

9. The system according to claim 8, wherein the second interface is a smartphone, a tablet, or a computer.

10. The system according to claim 8, wherein the second interface and the blood treatment machine are wirelessly connected.

11. The system according to claim 8, wherein the second interface comprises a processor, a signal transmitter, and a signal receiver, wherein the signal transmitter of the second interface is operable to send signals to the blood treatment machine and the signal receiver of the second interface is operable to receive signals from the blood treatment machine.

12. The system according to claim 11, wherein the processor of the second interface is configured to generate an alert.

13. The system according to claim 12, wherein the alert is a visual alert displayed on the second interface.

14. The system according to claim 12, wherein the alert is an auditory alert from a speaker of the second interface.

15. The system according to claim 12, wherein the alert is a vibrational alert and at least part of the second interface is configured to vibrate when the processor generates the alert.

16. The system according to claim 12, wherein the alert of the second interface indicates an upcoming blood measurement will occur in an amount of time.

17. The system according to claim 16, wherein the amount of time is less than 1 minute.

18. The system according to claim 1, wherein the blood treatment machine comprises the timer.

19. The system according to claim 1, wherein the blood monitoring device comprises the timer.

20. The system according to claim 1, wherein the controller is configured so that the operator can see parameters of the notification.

21. A blood treatment machine comprising:
a receiver configured to receive blood pressure data from a blood pressure monitor when the blood pressure monitoring device is connected to the blood treatment machine,
a user interface configured to display information related to the blood pressure data received by the receiver, and
a controller configured to generate a notification, based on data received from a timer, to notify a user of an upcoming blood pressure measurement before the blood pressure measurement occurs.

22. A method for notifying an operator of a blood treatment machine that a blood pressure measurement is about to occur, the method comprising:
placing a blood pressure monitoring device for measuring blood pressure on a patient,
receiving data from a timer,
based on the data received from the timer, notifying the operator of the blood treatment machine that the blood pressure measurement is about to occur, and
measuring the blood pressure of the patient.

* * * * *

UNITED STATES PATENT AND TRADEMARK OFFICE
CERTIFICATE OF CORRECTION

PATENT NO. : 10,515,534 B1
APPLICATION NO. : 16/012360
DATED : December 24, 2019
INVENTOR(S) : David Yuds and Martin Joseph Crnkovich Page 1 of 1

It is certified that error appears in the above-identified patent and that said Letters Patent is hereby corrected as shown below:

In the Claims

<u>Claim 6</u>
Column 10, Line 45, delete "time less" and insert --time is less--.

<u>Claim 8</u>
Column 10, Line 51, delete "connected the" and insert --connected to the--.

Signed and Sealed this
Twenty-fifth Day of February, 2020

Andrei Iancu
*Director of the United States Patent and Trademark Office*